United States Patent [19]

Shima et al.

[11] Patent Number: 5,371,273

[45] Date of Patent: Dec. 6, 1994

[54] PROCESS FOR PRODUCING METHYL METHACRYLATE

[75] Inventors: Yoshikazu Shima; Takafumi Abe; Hirofumi Higuchi, all of Niigata, Japan

[73] Assignee: Mitsubishi Gas Chemical Company, Inc., Tokyo, Japan

[21] Appl. No.: 135,066

[22] Filed: Oct. 12, 1993

[30] Foreign Application Priority Data

Nov. 16, 1992 [JP] Japan .................. 4-305542

[51] Int. Cl.$^5$ .............................................. C07C 67/00
[52] U.S. Cl. .................................................. 560/212
[58] Field of Search ......................................... 560/212

[56] References Cited

U.S. PATENT DOCUMENTS

| | | | |
|---|---|---|---|
| 5,068,399 | 11/1991 | Naito et al. | 560/212 |
| 5,075,493 | 12/1991 | Shima et al. | 560/212 |
| 5,087,736 | 2/1992 | Higuchi et al. | 560/215 |
| 5,250,729 | 10/1993 | Abe et al. | 562/599 |

*Primary Examiner*—José G. Dees
*Assistant Examiner*—Porfirio Nazario-Gonzalez
*Attorney, Agent, or Firm*—Frishauf, Holtz, Goodman & Woodward

[57] ABSTRACT

There is disclosed a process for producing methyl methacrylate through gas-phase catalytic reaction of methyl α-hydroxyisobutyrate which comprises feeding methanol in an amount by weight of 0.1 to 3.0 times the methyl α-hydroxyisobutyrate in a reactor along therewith and proceeding with the reaction at a reaction temperature in the range of 230° to 300° C. by the use of a transition-type synthetic faujasite zeolite having a specific lattice constant and a specific Na content (Na-/Al) as the catalyst. The process is capable of stably producing the objective product having excellent quality in high yield for a long period of time while preventing the problems of early deterioration of the catalyst and coloring of reaction product.

16 Claims, No Drawings

PROCESS FOR PRODUCING METHYL METHACRYLATE

BACKGROUND OF THE INVENTION

1. Field of the Invention

The present invention relates to a process for industrially producing methyl methacrylate by the use of methyl α-hydroxyisobutyrate as the starting raw material. Methyl methacrylate has industrially significant uses, for example, as the starting raw material for poly(methyl methacrylate) which is excellent in weather resistance and transparency, those for a variety of methacrylic acid esters, and the like.

2. Description of the Related Arts

The present inventors provided in Japanese Patent Application Laid-Open No. 196,753/1990, a process for producing an α-or β-unsaturated carboxylic acid ester by subjecting an α-hydroxycarboxylic acid ester or an α-or β-alkoxycarboxylic acid ester alone or the mixture thereof as starting raw materials to dehydration or dealcoholization reaction by the use of a crystalline aluminosilicate as the catalyst. Among the crystalline aluminosilicates used in the above-mentioned process, type-X or type-Y zeolite exhibited particularly excellent catalytic-activity. There are also disclosed that the crystalline aluminosilicate modified with an alkali metal and/or a platinum group element, especially type-X or type-Y zeolite is particularly effective as the catalyst in Japanese Patent Application Laid-Open No. 167,155/1991, 167,156/1991 and 167,157/1991.

As a result of further investigation based on the above-mentioned information, it has been found that such problems have been raised by the use of as the catalyst, ordinary type-X or type-Y zeolite or type-X or type-Y zeolite modified with an alkali metal and/or a platinum group element that the catalyst considerably deteriorates in a short period depending on the reaction conditions, thus requiring frequent regeneration thereof and besides the coloring phenomenon of the reaction liquid makes it difficult to separate the coloring substance from the objective product, thereby increasing the burden on the product purification step.

The early deterioration of the catalyst which participates in the reaction makes it impossible to continue the reaction after several days to a few months from the start of the reaction depending upon the reaction conditions. The deteriorated catalyst can be regenerated by firing it at a temperature higher than the reaction temperature, but frequent regeneration procedure is not favorable from the standpoint of industrial stabilized operation. In addition, the coloring substance appearing in the reaction liquid has a boiling point close to that of methyl methacrylate and a strong affinity therefor, and hence the substance can not easily be removed by separation through the procedure of distillation, extraction or the like. On the other hand, further improvement in the quality of methyl methacrylate as the product has increasingly been desired with the recent trend directed to the higher quality and sophistication not only in the field of special purpose including optical fiber but also in the field of general purpose such as molding material, extrusion plates, casting plates and coating materials. Accordingly, it is strongly required to suppress during the course of reaction the formation of the coloring substance.

SUMMARY OF THE INVENTION

It is an object of the present invention to provide a process capable of stably producing methyl methacrylate having excellent quality in high yield for a long duration of time while preventing the above-mentioned problems such as the early deterioration of the catalyst and the coloring of the reaction liquid.

Under such circumstances, intensive research and investigation were made by the present inventors in order to solve the above-mentioned problems. As a result, it has been ascertained by the present inventors that the early deterioration of the catalyst in the case of synthesizing methyl methacrylate through the gas-phase dehydration reaction by the use of methyl α-hydroxyisobutyrate as the reactive substrate and zeolite as the catalyst is due to the formation of high boiling byproducts which covers the port inlets of the zeolite as the catalyst and that the colored reaction liquid is attributable to the formation of biacetyl compounds as the main components. Thence, further investigation was made by the present inventors on the method of suppressing the formation of the high boiling byproducts as well as biacetyl compounds as the coloring substance. As a result, it has been found out by the present inventors that the formation of the biacetyl compounds and the high boiling by products can be suppressed, thus enabling the catalyst activity to be maintained for a long period of time by using methanol as the stabilizer at a temperature within a given range and at the same time, a transition type synthetic faujasite zeolite having a specific lattice constant and a specific Na content as the catalyst. The present invention has been accomplished on the basis of the aforesaid finding.

Specifically the present invention relates to a process for producing methyl methacrylate through gas-phase catalytic reaction by the use of methyl α-hydroxyisobutyrate as the starting raw material and synthetic faujasite zeolite as the catalyst in a fixed bed which process comprises feeding methanol in an amount by weight of 0.1 to 3.0 times the methyl α-hydroxyisobutyrate in a reactor along therewith and proceeding with the reaction at a reaction temperature in the range of 230° to 300° C. by the use of a transition type synthetic faujasite zeolite having a lattice constant in the range of 24.80 to 24.94 Å and an Na content in the range of 0.90 to 1.02 expressed in terms of Na/Al atomic ratio as the catalyst.

DESCRIPTION OF PREFERRED EMBODIMENT

In the following the present invention will be described in detail.

The synthetic faujasite zeolite to be used as the catalyst in the present invention is classified generally into type X and type Y, which have the same crystalline structure but have each different chemical-composition in terms of Si/Al atomic ratio. With regard to the more strict classification of synthetic faujasite zeolite, there is known the method in which it is classified into type X, transition type and type Y as described in E. Dempsey, G. H. Kuehl, D. H. Olson, "J. Phys. Chem., 73,387(1969).

The synthetic faujasite zeolite has a lattice constant which can be in the range of 24.6 to 25.1 Å and the number of Al atoms per unit lattice which can be in the range of 48 to 96, and is classified, with respect to the point of discontinuity for the linear relationship between unit lattice constant and Si/Al atomic ratio as determined by X-ray diffraction, into a transition type having a lattice constant of 24.80 to 24.94 Å, that is, the number of Al atoms per unit lattice of 64 to 80; type X having a range of lattice constant larger than said upper limit; and type Y having a range of lattice constant smaller than said lower limit.

The suitable synthetic faujasite zeolite to be used in the process according to the present invention is that of a transition type, that is, having a lattice constant of 24.80 to 24.94 Å. The characteristics of the faujasite zeolite as a catalyst are evaluated by Si/Al atomic ratio in many cases. However, it is reasonable to investigate those paying attention to the lattice constant from the viewpoint of precision of measurement in the case where a large amount of binders and/or noncrystalline portions are contained therein. Detailed investigation was made by the present inventors on the influence of the lattice constant of synthetic faujasite zeolite upon the gas-phase dehydration reaction of methyl α-hydroxyisobutyrate. As a result, it has been proved that the catalytic activity tends to be enhanced with an increase in the lattice constant but the catalyst durability tends to deteriorate therewith and that the transition type, i.e. that having a lattice constant in the range of 24.80 to 24.94 Å can establish the catalyst capable of suppressing the formation of biacetyl compounds and having a high catalytic activity and besides a long service, life of catalyst.

The transition type synthetic zeolite to be used as the catalyst in the process according to the present invention is that of type Na having an Na/Al atomic ratio of 0.90 to 1.02, preferably 0.92 to 1.02. In general, a zeolite of proton type or of polyvalent cation exchange type each having strong acidity is used as the catalyst for dehydration reaction of alcohols. However, it is unfavorable to use the catalyst having strong acidity in the dehydration reaction of methyl α-hydroxyisobutyrate according to the present invention, since the strong acidity causes de-hydrogenation reaction to take place simultaneously increasing the formation of acetone and/or biacetyl compounds and furthermore, increases the formation of high boiling byproducts such as dimethyl ether and polymethylbenzene derived from the methanol to be added to the reaction system as the stabilizer. Differing from the catalyst used in the conventional dehydration of an alcohol, the zeolite catalyst to be employed in the process according to the present invention is required for that the acid strength of zeolite be adjusted with a definite amount of Na. The acid point in zeolite is attributable to Al in the crystal lattice and thus the acid strength can be regulated to a level well suited to the gas-phase dehydration reaction of methyl α-hydroxyisobutyrate by introducing Na atoms in the crystal lattice in an amount almost equivalent to the Al in the lattice.

An Na/Al atomic ratio less than 0.90 results in an excessive acid strength, whereas that more than 1.02 leads to unreasonably low acid strength causing the problems that the conversion efficiency of methyl α-hydroxyisobutyrate is lowered and the relative proportion of the formation of methacrylic acid and high boiling byproducts is increased by Na as a base.

In addition, the Na atoms in a proportion ranging from 0.90 to 1.02 in terms of atomic ratio are presumed to not only exert the effect on the regulation of catalyst acidity but also play the catalytic function as the base point.

In more detail, it is thought that the adsorption condition of methyl α-hydroxyisobutyrate onto the type-Na faujasite zeolite is of so-called two-point adsorption type, the acid point of the zeolite and the base point thereof act on the hydroxyl groups of methyl α-hydroxyisobutyrate and the hydrogen atoms of the methyl groups, respectively, thus synergistically proceeding with the dehydration reaction and therefore, the reaction of the two-point adsorption type lowers the activation energy and enables methyl α-isohydroxyisobutyrate to undergo dehydration reaction at a relatively mild reaction conditions including a reaction temperature of 230° to 300° C. The success in attaining low-temperature reaction contributes to the enhancement of reaction selectivity and extension of the catalyst service life.

Since the synthetic faujasite zeolite to be used in the process according to the present invention is in the form of fine powder in itself, making it difficult to be used as such as the industrial catalyst in a fixed bed, it is made into a molding in the form of sphere, column or an other suitable form when used. In the case of producing the zeolite molding, the lack of mutual bondability among its fine powders necessitates the use of a binder to impart moderate plasticity and strength to the molding.

The binder to be used in the process of the present invention is a clay containing Al in a small amount, preferably less than 5% by weight. A silica-magnesia-based clay is particularly preferable, as it is well suited for suppressing the byproduction of biacetyl compounds as the coloring substances. Examples of the silica-magnesia-based clay containing a small amount of Al include talc, saponite, hectolite, sepiolite, and minesotite, among which synthetic hectolite is particularly suitable.

There are known, as a general-purpose binder, kaolin, montomorillonite, bentonite and Portland cement. However, the clay to be used in combination with the transition-type synthetic faujasite zeolite in the present invention not only exerts the effect as the binder but also greatly contributes to the suppression of the byproduction of biacetyl compounds as the coloring substances.

Depending on the type, the amount of the clay to be added to the zeolite for molding the catalyst in the present invention can be the amount usually added to zeolite, and is preferably in the range of 5 to 30% by weight based on the molding taking into consideration the ease of molding, mechanical strength of the molding and the like. In order to improve the moldability, there can be added to the clay a molding assistant or a lubricant such as carboxymethyl cellulose, stearic acid, an alcohol and a surfactant.

The adoptable method of molding the catalyst can be any of various methods including extrusion, rolling granulation, tabletting molding, etc. depending on the shape of the molding required.

As described hereinbefore, it is made possible to produce the catalyst capable of minimizing the byproduction of biacetyl compound and extending the service life thereof by virtue of setting the reaction temperature in the range of 230° to 300° C., using methanol as the stabilizer and defining Na content in the transition-type synthetic faujasite zeolite to regulate the strength of acidity of the zeolite. In addition, it becomes possible to further enhance the effect on suppressing the formation of biacetyl compounds by adopting a catalyst preparation method in which the zeolite is molded with a clay free from Al and the acid points due to Al on the outside surface of the catalyst are minimized.

Methyl α-hydroxyisobutyrate to be used as the starting raw material in the present invention is produced by the methanolysis of α-hydroxyisobutyramide or, as described in Japanese Patent Publication No. 2874/1990, by the reaction of α-hydroxyisobutyramide with methyl formate. Moreover, methyl α-hydroxyisobutyrate is obtained from the high boiling byproducts in so-called ACH process wherein methyl methacrylate is produced from acetone cyanohydrin and sulfuric acid and those in $C_4$ oxidation process wherein isobutylene is employed as the starting raw material. The methyl α-hydroxyisobutyrate which is recovered from such a high boiling byproduct usually contains methyl α- or β-methoxyisobutyrate. The catalyst in the present invention, however, is effective also for demethanolizing reaction of such homologues and thus, the homologues can be recovered as methyl methacrylate as well by the effect of the catalyst.

As the reaction in the process according to the present invention belongs to gas-phase reaction by the use of fixed-bed catalyst, methyl α-hydroxyisobutyrate as the starting raw material is vaporized by preheating and then fed in a reactor. The vaporized material may be introduced therein alone or in combination with a diluting inert gas such as nitrogen argon and helium. However, it is preferable to use methanol as the diluent in order to enhance the yield of methyl methacrylate and at the same time, suppress the byproduction of biacetyl compounds as coloring substances. The proportion of methanol to be used as the diluent is 0.1 to 3.0 times, preferably 0.2 to 2.0 times by weight the methyl α-hydroxyisobutyrate. In regard to the feed velocity of the starting raw material, the weight-based hourly space velocity is in the range of 0.1 to 5.0 $hr^{-1}$, preferably 0.2 to 3.0 $hr^{-1}$, on the basis of the total weight of methyl α-hydroxyisobutyrate as the starting raw material and methanol as the diluent per unit weight of the catalyst.

Proper setting of the reaction temperature is also important in the process of the present invention in order to suppress the byproduction of high boiling byproducts and biacetyl compounds. The reaction temperature can be maintained at a constant temperature in the range of 230° to 300° C., but is preferably raised gradually in a specific range with the elapse of time of reaction so as to maintain the conversion efficiency of methyl α-hydroxyisobutyrate in the range of 98.0 to 99.9% in order to suppress the formation of various byproducts and at the same time, keep the catalyst activity at a proper level. A conversion efficiency thereof less than 98.0% leads to decrease in the selectivity to the objective methyl methacrylate due to increase in the formation of methacrylic acid and high boiling substances, whereas that more than 99.9% resulting from the reaction at an unnecessarily high temperature accelerates decompositional reaction of the starting raw material and the reaction products, thereby lowering the yield of methyl methacrylate and limiting the service life of the catalyst. The reaction is initiated at a temperature in the range of 230° to 270° C., preferably 240° to 260° C., and is completed at a temperature in the range of 250° to 300° C., preferably 260° to 290° C. The reaction pressure is not specifically limited, but is usually equal to or somewhat higher than atmospheric pressure.

The above-mentioned regulation of reaction temperature in the process of the present invention is necessary to compensate for the decrease with the elapse of time in the activity points due to the adhesion of high boiling byproducts to the catalyst. When it is made impossible to maintain the conversion efficiency of methyl α-hydroxyisobutyrate in the range of 98.0 to 99.9% in the above-mentioned temperature range, the feed of the starting raw material is interrupted and thereafter, the catalyst is fired in the air at a temperature at which the faujasite zeolite is not destroyed, preferably at 550° C. or lower. By the aforesaid procedure, the catalyst activity can be restored almost completely, thereby facilitating regeneration and repeated use of the catalyst of the present invention.

The reaction liquid product obtained through the process of the present invention contains unreacted starting-raw-material and such byproducts as methacrylic acid, acetone, biacetyl compounds and polymethylbenzene in addition to the objective methyl methacrylate. Such byproducts other than the biacetyl compounds can easily be separated by the ordinary purification method such as distillation, extraction or the like.

The biacetyl compounds with a concentration of higher than 500 ppm in the reaction liquid can be removed as low boiling distillate by the ordinary distillation without causing any problem, while those with a concentration of higher than 500 ppm necessitates the use of high-performance superfractionation requiring several tens of plates or a removal step such as treatment with chemicals or a catalyst, thus causing increase in facility cost and/or energy cost and decrease in the recovery rate of the objective product. Nevertheless, the use of the catalyst according to the present invention enables suppression of biacetyl compounds as byproducts as low as the allowable level as well as the production of the objective methyl methacrylate with high purity by assuring a high yield of methyl methacrylate.

By using methyl α-hydroxyisobutyrate as the starting raw material, methanol as the stabilizer and transition-type synthetic faujasite zeolite having a prescribed amount of Na as the fixed-bed catalyst and setting the reaction temperature in the range of 230° to 300° C., the process according to the present invention enables the reaction product to be prevented from coloring and methyl methacrylate to easily be purified and produced in high yield over a long period of time, thus rendering itself highly valuable in the related industrial fields.

In the following, the present invention will be described in more detail with reference to examples, which however shall not be construed to limit the scope of the present invention thereto.

EXAMPLE 1

1) Preparation of catalyst: NaOH in an amount of 75.9 g was dissolved in 462.9 g of ion-exchanged water. The resultant solution was incorporated with 27.7 g of sodium aluminate (51% by weight of $Al_2O_3$ and 36% by weight of $Na_2O$) and further the mixed liquid of 333.0 g of silica sol (20% by weight of $SiO_2$) and 200.0 g of ion-exchanged water under sufficient stirring until a homogeneous mixed slurry was obtained. The resultant mixture was placed in an autoclave and crystallized at 100° C. for 48 hours. Then, the crystallized product was allowed to cool to room temperature, filtered, washed with water to pH 10.2, dried at 110° C. and calcined at 500° C. to afford 51.6 g of zeolite anhydride. As the results of X-ray diffraction and analysis for chemical composition, the zeolite anhydride was confirmed as faujasite zeolite having a lattice constant of 24.86 Å and an Na/Al atomic ratio of 0.96.

The zeolite thus obtained in an amount of 20.1 g was incorporated with 5.06 g of Laponite RD (produced by Laporte Corp.) and 1.25 g of crystalline cellulose, followed by gradual addition of 14 g of ion-exchanged water with sufficient kneading. Subsequently, the kneaded product was extrusion-molded, dried at 110° C. and calcined at 500° C. to afford 25 g of molded columnar catalyst with 1.2 mm diameter and 3 to 7 mm length.

2) Reaction: A quartz glass tube with 15 mm inside diameter and 450 mm length was packed with 10 g of the above molded catalyst to form a catalyst bed, the temperature of which was kept at 250° C. Then, 50% by weight solution of methyl α-hydroxyisobutyrate in methanol was fed in the catalyst bed via a preheating bed at a rate of 10 g/hr to gasify the solution. The reaction gas after 8 hours from the start of the reaction was condensed by cooling and the resultant condensate was sampled for one (1) hour. The result of analysis of the sample by GC (gas chromatography) gave a conversion efficiency of methyl α-hydroxyisobutyrate of 99.5%, a selectivity to the objective methyl methacrylate of 93.4%, a selectivity to methacrylic acid of 2.2% and a biacetyl concentration in the reaction liquid of 120 ppm.

Thereafter, the reaction temperature was gradually raised so as to maintain the conversion efficiency of methyl α-hydroxyisobutyrate in the range of 99.0 to 99.9% over a period of one month until it reached 280° C. The result of analysis of the product sample gave a conversion efficiency of methyl α-hydroxyisobutyrate of 99.6%, a selectivity to methyl methacrylate of 91.8% and a biacetyl concentration in the reaction liquid of 180 ppm. The reaction was further continued at 280° C. and ceased after 3 days.

Subsequently, nitrogen was passed through the reaction system at 350° C. and then gradually replaced with air so as not to cause a hot spot to regenerate the catalyst by firing it at 400° C. for 12 hours. After the regeneration of the catalyst, the reaction was resumed at a catalyst bed temperature of 250° C. at the same feed rate of the starting raw material. After 8 hours from the resumption, the objective methyl methacrylate was obtained at a selectivity thereto of 93.1% at a conversion efficiency of methyl α-hydroxyisobutyrate of 99.6%.

EXAMPLES 2 AND 3 AND COMPARATIVE EXAMPLES 1 AND 2

Various faujasite-zeolite catalysts each having a different lattice constant were prepared by altering the chemical composition of the raw materials for the catalyst. The procedure in Example 1 was repeated to proceed with the reaction except that the temperatures at the start and the end of the reaction were varied so as to maintain the conversion efficiency of methyl α-hydroxyisobutyrate in the range of 99.0 to 99.9%. The results are given in Table 1 along with the results obtained in Example 1.

TABLE 1

|  | Lattice constant (Å) | Reaction time (day) | Reaction temperature(°C.) start/end | MMA yield (mol %) | Biacetyl concentration (ppm) |
| --- | --- | --- | --- | --- | --- |
| Example 1 | 24.86 | 33 | 250/280 | 91.4 | 180 |
| Example 2 | 24.80 | 21 | 255/285 | 90.3 | 230 |
| Example 3 | 24.91 | 37 | 250/280 | 91.1 | 180 |
| Comparative Example 1 | 24.73 | 6 | 280/290 | 82.3 | 740 |
| Comparative Example 2 | 25.00 | 12 | 240/290 | 83.5 | 460 |

Remark: MMA: methyl methacrylate

EXAMPLES 4 AND 5 AND COMPARATIVE EXAMPLES 3 AND 4

Various faujasite-zeolite catalysts each having a different Na/Al atomic ratio were prepared by altering the washing conditions such as the amount of water. The procedure in Example 1 was repeated to proceed with the reaction except that the reaction temperature was set constant at 270° C., and the chemical composition of the raw materials for the catalyst and the temperature in evaluating the catalyst were altered. After 48 hours from the start of the reaction, the yield of methyl methacrylate and the concentration of biacetyl compounds were analyzed by means of GC. The results are given in Table 2.

TABLE 2

|  | Na/Al (atomic ratio) | Conversion efficiency (%) | MMA yield (mol %) | Biacetyl concentration (ppm) |
| --- | --- | --- | --- | --- |
| Example 4 | 0.93 | 100 | 88.5 | 350 |
| Example 5 | 1.02 | 100 | 88.3 | 260 |
| Comparative Example 3 | 0.80 | 100 | 81.4 | 1680 |
| Comparative Example 4 | 1.11 | 69.5 | 65.1 | 120 |

EXAMPLES 6 AND 7 AND COMPARATIVE EXAMPLE 5

The procedure in Example 1 was repeated to prepare molded catalyst except that the Laponite RD was replaced with an other type of clay as the binder. The evaluation of the catalyst was carried out in the same manner as in Examples 4 and 5. The results are given in Table 3 along with the results obtained in Example 5.

TABLE 3

|  | Clay | Clay composition (wt %) | | | MMA yield (mol %) | Biacetyl concentration (ppm) |
| --- | --- | --- | --- | --- | --- | --- |
|  |  | $SiO_2$ | MgO | $Al_2O_3$ |  |  |
| Example 5 | Laponite RD | 59.5 | 27.3 | — | 88.3 | 260 |
| Example 6 | Miraclay | 50.8 | 16.8 | 1.8 | 87.4 | 280 |
| Example 7 | SWN | 54.3 | 27.9 | 0.4 | 88.0 | 240 |
| Comparative Example 5 | Bentonite A | 75.8 | 1.6 | 13.7 | 83.2 | 1510 |

Remarks:
Miraclay; natural sepiolite (produced by Ohmi Mining Industries Co., Ltd.)
SWN; synthetic smectite (produced by Cope Chem. Corp.)

COMPARATIVE EXAMPLE 6

The procedure in Example 1 was repeated except that methanol was not added to methyl α-hydroxyisobutyrate and nitrogen was passed through the reaction system from the inlet of a preheater at a rate of 100 ml/min. After 48 hours from the start of the reaction, the analysis results showed a conversion efficiency of methyl α-hydroxyisobutyrate of 99.8%, a selectivity to methyl methacrylate of 62.2% and a selectivity to methacrylic acid of 20.3%. After 120 hours therefrom, the conversion efficiency of methyl α-hydroxyisobutyrate was lowered as low as 80% and thus, the reaction was ceased.

What is claimed is:

1. A process for producing methyl methacrylate by a gas-phase catalytic reaction of methyl α-hydroxyisobutyrate as the starting raw material, which process comprises feeding the methyl α-hydroxyisobutyrate and methanol, the methanol being in an amount by weight of 0.1 to 3.0 times the amount of the methyl α-hydroxyisobutyrate, in a reactor at a reaction temperature of 230° to 300° C. in the presence of a catalyst, said catalyst comprising a transition-type synthetic faujasite zeolite having a lattice constant of 24.80 to 24.94 Å and an Na content of 0.9 to 1.02 expressed in terms of Na/Al atomic ratio.

2. The process according to claim 1 wherein said zeolite is made into a molding by the use of a clay having an Al content of less than 5% by weight.

3. The process according to claim 2 wherein said clay is synthetic hectolite.

4. The process according to claim 2 wherein said clay is added in the molding in an amount of 5 to 30% by weight based on the molding.

5. The process according to claim 1 wherein the gas-phase catalytic reaction is carried out at a weight-based hourly space velocity of 0.1 to 5.0 $hr^{-1}$.

6. The process according to claim 1 wherein the temperature at the start of the gas-phase catalytic reaction is 230° to 270° C., the temperature at the end of said reaction is 250° to 300° C. and the reaction temperature is regulated so as to maintain a conversion efficiency of the methyl α-hydroxyisobutyrate of 98.0 to 99.9%.

7. The process according to claim 1 wherein the zeolite has a Na/Al atomic ratio of 0.92 to 1.0.

8. The process according to claim 1 wherein the methanol is in an amount of 0.2 to 2 times the methyl α-hydroxyisobutyrate.

9. The process according to claim 1 wherein the gas-phase catalytic reaction is carried out at a weight-based hourly space velocity of 0.2 to 3 $hr^{-1}$.

10. The process according to claim 2 wherein the clay is a silica-magnesia clay.

11. The process according to claim 2 wherein the clay is selected from the group consisting of talc, saponite, hectolite, sepiolite and minesotite.

12. The process according to claim 2, wherein the methanol is in an amount of 0.2 to 2 times the methyl α-hydroxyisobutyrate; the zeolite has a Na/Al atomic ratio of 0.92 to 1.02; and the gas-phase catalytic reaction is carried out at a weight-based hourly space velocity of 0.2 to 3 $hr^{-1}$.

13. The process according to claim 10 wherein the clay is synthetic hectolite.

14. The process according to claim 1 wherein the lattice constant is 24.86 Å and the Na/Al atomic ratio is 0.96.

15. The process according to claim 1 wherein the lattice constant is 24.80 Å.

16. The process according to claim 1 wherein the lattice constant is 24.91 Å.

* * * * *